United States Patent [19]

Lee

[11] Patent Number: 4,612,398
[45] Date of Patent: Sep. 16, 1986

[54] ALKYL MERCAPTAN PROCESS

[75] Inventor: John Y. Lee, Baton Rouge, La.

[73] Assignee: Ethyl Corporation, Richmond, Va.

[21] Appl. No.: 604,892

[22] Filed: Apr. 27, 1984

[51] Int. Cl.⁴ .......................................... C07C 148/00
[52] U.S. Cl. ...................................... 568/73; 568/72; 568/61
[58] Field of Search ................. 568/72, 73, 61, 59, 568/60

[56] References Cited

U.S. PATENT DOCUMENTS

| | | | |
|---|---|---|---|
| 2,052,268 | 8/1936 | Williams et al. | 568/60 |
| 2,434,510 | 1/1948 | Olin | 568/72 |
| 2,443,852 | 6/1948 | Eaton et al. | 568/72 |
| 3,036,133 | 5/1962 | Goshorn et al. | 568/60 |
| 3,257,464 | 6/1966 | Buchholz et al. | 568/60 |

FOREIGN PATENT DOCUMENTS

| | | | |
|---|---|---|---|
| 0501697 | 4/1954 | Canada | 568/73 |
| 0501698 | 4/1954 | Canada | 568/73 |

*Primary Examiner*—Donald G. Daus
*Assistant Examiner*—Mary E. Ceperley
*Attorney, Agent, or Firm*—Donald L. Johnson; John F. Sieberth; Joseph D. Odenweller

[57] ABSTRACT

A process for making alkyl mercaptans in high yield while minimizing the formation of dialkyl sulfides is conducted by reacting an olefin with hydrogen sulfide in an inert solvent (e.g. $CH_2Cl_2$) containing a Lewis Acid catalyst (e.g. $BF_3$). Best results are obtained when the olefin is added to the hydrogen sulfide solution at a rate that keeps the amount of unreacted olefin below about 0.05 moles per mole of hydrogen sulfide.

9 Claims, No Drawings

ALKYL MERCAPTAN PROCESS

BACKGROUND OF THE INVENTION

Alkyl mercaptans are useful in the manufacture of alkyl sulfonic acids which are used to make detergents such as those described in U.S. Pat. No. 2,142,162 and U.S. Pat. No. 2,187,339. Alkyl mercaptans are readily converted to sulfonic acid by oxidation. Oxidation of mercaptans with nitric acid is described in Werniz, U.S. Pat. No. 2,142,162; U.S. Pat. No. 2,187,338 and U.S. Pat. No. 2,187,339. Proell, et al U.S. Pat. No. 2,505,910 disclose a method of oxidizing mercaptans to sulfonic acids using oxygen in combination with nitrogen oxides. Schreyer et al U.S. Pat. No. 4,052,445 discloses an oxidation process using hydrogen peroxide as the oxidant.

Alkyl mercaptans had been made by the reaction of hydrogen sulfide with olefins. Olin, U.S. Pat. No. 2,434,510 describes a process for reacting hydrogen sulfide and olefin by passing the mixture containing a Lewis Acid catalyst through a tubular reactor or by a batch method in which hydrogen sulfide is added to a reactor containing the olefin and catalyst.

Eaton et al, U.S. Pat. No. 2,443,852 describes a similar process carried out under pressure in which the olefin, hydrogen sulfide and catalyst are concurrently mixed in the liquid phase and then the hydrogen sulfide is vaporized to cool the reaction mixture.

Although the reaction of hydrogen sulfide with olefin does yield alkyl mercaptans, it also forms dialkyl sulfides by reaction of an alkyl mercaptan with olefin. Alkyl mercaptans are readily oxidized to sulfonic acid but dialkyl sulfides are not. Therefore, a need exists for a process that will make alkyl mercaptans in high yield while minimizing the formation of dialkyl sulfides.

SUMMARY OF THE INVENTION

It has now been discovered that alkyl mercaptans can be made in high yield with minimal formation of dialkyl sulfide by-product by feeding an olefin to a solution of $H_2S$ in an inert organic solvent containing a catalytic amount of a Lewis Acid catalyst.

DESCRIPTION OF THE PREFERRED EMBODIMENT

A preferred embodiment of the invention is a process for making an alkyl mercaptan by the reaction of an olefin with hydrogen sulfide while minimizing the formation of dialkyl sulfide, said process comprising reacting about 5–50 moles of hydrogen sulfide with a mole of olefin in an inert organic solvent containing a Lewis Acid catalyst.

Inert solvents that can be used include any organic liquid that will dissolve a substantial amount of the $H_2S$ and will not react with the $H_2S$, the olefin reactant or any of the products. Suitable solvents include carbon disulfide and aliphatic and aromatic halohydrocarbons. Preferably, the solvent should have a normal boiling point within the range of about 0°–200° C. Examples of these solvents are chlorobenzene, dichlorobenzene, methylene dichloride, chloroform, carbontetrachloride, ethyl chloride, 1,2-dichloroethane, 1,1-dichloroethane, 1,1,1-trichloroethane, 1,1,2-trichloroethane, sym-tetrachloroethane and 1,1,1,2-tetrachloroethane and the like including mixtures thereof.

Of these, the aliphatic halohydrocarbons are preferred. Most work has been conducted using methylene chloride as the solvent.

The amount of solvent should be an amount which will dissolve a substantial portion of the $H_2S$ reactant under the pressure-temperature conditions. A useful range is about 1–20 parts by weight solvent per each part of $H_2S$. A preferred range is about 5–10 parts by weight solvent for each part $H_2S$.

The amount of $H_2S$ should be an amount in excess of the stoichiometric amount required to react with the olefin. Preferably, the amount of $H_2S$ is about 10–100 times the stoichiometric amount and more preferably about 15–30 times the stoichiometric amount.

The solvent and $H_2S$ are placed in a reaction vessel. Preferably the reaction vessel is capable of withstanding pressures up to about 500 psig. In order to avoid fires or explosions, the reaction vessel should be purged with an inert gas such as nitrogen prior to charging the hydrogen sulfide.

The reaction is catalyzed by a Lewis Acid such as $AlCl_3$, $BF_3$, $BCl_3$, $FeCl_3$, $SnCl_4$, $ZnCl_2$, $GaCl_3$ and the like. The most preferred catalyst is $BF_3$. Only a catalytic amount is required. A useful range is about 0.1–3 wt% based on the solvent and hydrogen sulfide. Good results have been obtained using about 1–2 wt% $BF_3$.

The catalyst can be all added to the solvent and hydrogen sulfide at the start of the reaction or it can be fed during the course of the reaction. Preferably, all or most of the catalyst is added prior to olefin feed.

The order of addition of the catalyst to the reaction zone is not critical. It can be added after the hydrogen sulfide or before the hydrogen sulfide or concurrently with the hydrogen sulfide. Alternatively, it can be mixed with the olefin and fed to the reaction zone with the olefin. It is more convenient to add the catalyst to the reaction zone before the hydrogen sulfide. In the examples, all or most of the catalyst was added prior to olefin feed although it is possible that better results could be achieved by feeding fresh catalyst to the reaction zone during olefin feed.

The reaction temperature is preferably kept rather low. A useful temperature range is about −30° to 80° C. A preferred range is about −25° to 50° C. and more preferably −20° to 30° C.

Any olefinic hydrocarbon can be used in the process. Mono-olefins form mono-mercaptans whereas polyunsaturated olefins form polymercapto-substituted hydrocarbons. Preferably the olefin is a cyclic, branched or linear olefinic hydrocarbon containing about 4–30 carbon atoms such as 1-butene, 2-butene, isobutene, 1-pentene, 2-ethyl-1-hexene, isooctene (diisobutylene), tetrapropylene, 1-eicosene, 1-docosene, 1-triacontene, 8-octadecene, 9-eicosene, 10-tetracosene, cyclooctadiene, cyclohexene, limonene, butadiene, dicyclopentadiene and the like.

The preferred olefins are internal aliphatic olefins because these can be converted to superior surface active agents. Internal olefins can be readily made from commercially available olefins by isomerization following known procedures. Isomerization catalysts include Lewis Acids, sulfuric acid, sulfonic acid, sulfonic acid ion exchange resins and the like. Excellent results have been achieved by adding iron carbonyl to an α-olefin mixture which is high in vinylidene olefins and heating the mixture to about 170°–270° C.

Because of their utility in making very effective surfactants, the more preferred olefins are the internal olefins containing about 12–20 carbon atoms such as 6-dodecene, 7-tetradecene, 8-octadecene, 10-eicosene and the like.

The olefins are pumped into the reaction zone at a controlled rate such that the amount of unreacted olefin in the liquid hydrogen sulfide is maintained at a low level. In this manner, the effective stoichiometric excess of hydrogen sulfide over unreacted olefin is extremely high. Initially, this excess can be 100 theories or even higher. It is this feature that is believed responsible for the high yield of alkyl mercaptans and very low formation of dialkyl sulfides.

The olefin feed is controlled such that the mole ratio unreacted olefin to hydrogen sulfide in the reaction mixture does not exceed about 0.05:1.0 during the reaction. More preferably, the mole ratio of unreacted olefin to hydrogen sulfide does not exceed about 0.01:1.0 reaction mixture.

The olefin feed time will depend somewhat on the scale of the reaction. In the laboratory, feed times of 30 minutes have given good results. On a larger scale, feed times up to 8 hours or more could be used.

Following the olefin feed, the reaction mixture can be stirred for a short period to make sure all the olefin has reacted but this is generally not necessary with the controlled feed rate.

The reaction mixture can be water washed to remove catalyst. Conversions have been over 95% to a product that is over 80 wt% alkyl mercaptan and less than 20 wt% dialkyl sulfide. The product is usually over 90 wt% alkyl mercaptan and less than 10 wt% dialkyl sulfide. These two components can be separated by distillation if desired. Generally, the reaction mixture without further separation or purification can be subject to an oxidation process for conversion to sulfonic acid. Any required separation can readily be performed on the sulfonic acid.

The following example serves to illustrate how the process can be carried out.

EXAMPLE 1

This experiment was conducted for comparative purposes without a solvent.

In an autoclave was placed 157.47 g (0.803 moles) of internal tetradecene and 4.14 g of $BF_3$. Then $H_2S$ was passed into the stirred olefin at 28° C. raising the reactor pressure to about 250–260 psig. $H_2S$ feed was continued for about 20 minutes and then the reaction was stirred for two hours at 240–250 psig. It was then vented. The product was analyzed by NMR and gas chromatography (GC) as follows:

Unreacted olefin: 44%
Tetradecyl mercaptan: 39%
Dialkyl sulfides: 17%

EXAMPLE 2

This is another comparative example. In this example, 110.67 g of 7-tetradecene was placed in an autoclave and then excess $H_2S$ and 1.49 g of $BF_3$ were added over a ten minute period at 30° C. The mixture was heated to 54° C. for 1.5 hours and then de-gassed. The product was analyzed by GC as follows:

Unreacted olefin: 58%
Tetradecyl mercaptan: 31%
Dialkyl sulfide: 7%

EXAMPLE 3

This is an example of the process conducted in an inert solvent according to the present invention.

In an autoclave was placed 32.69 g 7-tetradecene, 117 g $CH_2Cl_2$, 1.49 g $BF_3$ and a stoichiometric excess of $H_2S$ to a pressure of 250 psig. In addition, about 14 g of dodecane was included as an internal GC standard. Initial temperature rose to 30°–34° C. and after 20 minutes dropped to 27° C. Samples were taken at 0.5, 1 and 2 hours and analyzed by GC as follows:

|  | Hours | | |
| --- | --- | --- | --- |
|  | 0.5 | 1.0 | 2.0 |
| tetradecyl mercaptan | 63% | 72% | 72% |
| dialkyl sulfide | 17% | 17–20% | 15–17% |

EXAMPLE 4

This run was also conducted in $CH_2Cl_2$ solvent. To an autoclave was charged 30 g 7-tetradecene, 116 g $CH_2Cl_2$, 1.5 g $BF_3$, 15.7 g dodecane and excess $H_2S$ to a pressure of 150 psig at 8° C. This mixture was stirred at 0° C. and samples taken periodically for analysis.

|  | Hours | | | |
| --- | --- | --- | --- | --- |
|  | 0.5 | 1.0 | 2.0 | 2.5 |
| tetradecyl mercaptan | 52 | 57 | 65 | 62 |
| dialkyl sulfide | 11 | 11 | 11 | 12 |

These results show that the reaction is very fast in a solvent giving 65 wt% product in 2 hours. In Example 1, only 39 wt% product had formed in the same time period.

EXAMPLE 5

To an autoclave was charged 70.0 g 7-tetradecene, 90 g carbon disulfide, 27.89 g dodecane, 1.4 g $BF_3$ and excess $H_2S$ to a pressure of 200 psig. The reaction was stirred 20 minutes at 34° C. and then analyzed by GC as follows:

Unreacted olefin: 37%
Tetradecyl mercaptan: 55%
Dialkyl sulfide: 5%

EXAMPLE 6

In an autoclave was placed 310 g of $CH_2Cl_2$ at 22° C. Then 50 g of $H_2S$ was dissolved in the $CH_2Cl_2$ causing the temperature to rise to 28° C. Then 2 g $BF_3$ and 14.9 g of 7-tetradecene was added over a 30 minute period. The mixture was analyzed by GC as follows:

Unreacted olefin: 0.6%
Tetradecyl mercaptan: 86%
Dialkyl sulfide: 11%

These results show that by the further modification of reverse addition of the olefin to the $H_2S$ in an inert solvent containing $BF_3$ catalyst, the conversion is almost complete in 30 minutes to produce a product that is 86% of the desired tetradecyl mercaptan.

I claim:

1. A process for making alkyl mercaptan by the reaction of an aliphatic mono-olefinic hydrocarbon containing 10–20 carbon atoms with hydrogen sulfide in a molar ratio of about 5–50 moles of hydrogen sulfide per mole of olefin in a liquid phase while minimizing the formation of dialkyl sulfides, said process comprising (a) forming a solution of hydrogen sulfide and a catalytic amount of a Lewis Acid in an inert solvent selected from carbon disulfide and aliphatic and aromatic halohydrocabons, (b) adding said olefin to the hydrogen sulfide solution at a rate such that the mole ratio of unreacted olefin to hydrogen sulfide does not exceed about 0.05:1.0 and at a temperature of about $-30°$ to $80°$ C. and (c) recovering said alkyl mercaptan product.

2. A process of claim 1 wherein said olefin is an internal olefin.

3. A process of claim 1 wherein said solvent is a saturated aliphatic or aromatic halohydrocarbon boiling in the range of $0°-200°$ C.

4. A process of claim 3 wherein said solvent is a polyhalomethane, a mono or polyhaloethane, a mono or polyhalopropane, a mono or polyhalobutane or mixtures thereof.

5. A process of claim 3 wherein said solvent is selected from dichloromethane, trichloromethane, carbon tetrachloride, ethylchloride, 1,2-di-chloroethane, 1,1-dichloroethane, 1,1,1-trichloroethane, 1,1,2-trichloroethane, symtetrachloroethane, 1,1,1,2-tetrachloroethane and mixtures thereof.

6. A process of claim 5 wherein said Lewis Acid is boron trifluoride.

7. A process of claim 1 wherein said olefin is added to said solution of hydrogen sulfide and Lewis Acid catalyst at a rate such that the mole ratio of unreacted olefin to hydrogen sulfide does not exceed about 0.01:1.0 during any substantial period during the reaction.

8. A process of claim 6 wherein said solvent is dichloromethane.

9. A process of claim 7 wherein said solvent is dichloromethane.

* * * * *